United States Patent [19]

Moser

[11] Patent Number: Plant 7,370

[45] Date of Patent: Oct. 30, 1990

[54] HIBISCUS PLANT NAMED HAWAIIAN HOLLY

[75] Inventor: Frank C. Moser, Alva, Fla.

[73] Assignee: Yoder Brothers, Inc., Barberton, Ohio

[21] Appl. No.: 396,960

[22] Filed: Aug. 21, 1989

[51] Int. Cl.[5] ..... A01H 5/00

[52] U.S. Cl. ..... Plt./54

[58] Field of Search ..... Plt./54

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Hibiscus plant named Hawaiian Holly particularly characterized by its scarlet red flower color with a darker red eye, regular flower form, flower 10 cm. in diameter, excellent pot habit, very compact growth, dark green leaves varying from heterophyllus to entire, flower life a single day, easy to propagate, excellent resistance to bacterial leaf spot (Pseudomonas sp.), excellent shipping tolerance (bud drop resistance).

2 Drawing Sheets

The present invention comprises a new and distinct cultivar of hibiscus, botanically known as *Hibiscus rosa-sinensis L.*, and referred to by the cultivar name Hawaiian Holly.

Hawaiian Holly, identified as 84-026-004 during the breeding and selection process, originated from a planned cross hybridization between two selected breeding lines in a controlled breeding program in Fort Myers, Fla. by Frank C. Moser.

The female, or seed parent is a breeding line designated as code #0005 and the pollen, or male parent is a breeding line designated as code #0002.

Hawaiian Holly was discovered and selected as a flowering plant within the progeny of the stated cross by Frank C. Moser in July of 1984, outside in ground beds in Fort Myers, Fla.

The first asexual reproduction of Hawaiian Holly was accomplished when vegetative cuttings were taken from the initial plant selection in October of 1984 in Fort Myers, Fla. from plants grown outside in ground beds, by technicians working under formulations established and supervised by Frank C. Moser.

Horticultural examinations of controlled flowerings of successive generations of plants derived from cuttings taken from the original selection have shown that the unique combination of characteristics as herein disclosed for Hawaiian Holly are fixed and retained through successive generations of asexual reproduction.

Hawaiian Holly has not been observed under all possible environmental conditions. The phenotype may vary significantly with variations in environment such as temperature and light intensity.

The following observations, measurements and comparisons describe plants that were grown in Fort Myers, Fla. in a controlled greenhouse environment and following a commercial schedule.

The following traits have been repeatedly observed and are determined to be basic characteristics of Hawaiian Holly, which, in combination, distinguish this Hibiscus as a new and distinct cultivar:

1. Scarlet-red flower color, with a darker red eye.
2. Regular flower form, with the flower being about 10 cm. in diameter.
3. Excellent pot habit, very compact growth.
4. Dark green leaves, varying from heterophyllus to entire.

5. Flower lift is a single day.
6. Easy to propagate.
7. Excellent resistance to bacterial leaf spot (Pseudomonas sp.).
8. Excellent shipping tolerance (bud drop resistance).

The accompanying photographic drawings show typical habit, flower and leaf characteristics of Hawaiian Holly, with colors being as nearly true as possible with illustrations of this type. Sheet 1 is a color photograph of Hawaiian Holly grown as a commercially finished pot plant. Sheet 2 is a black and white photograph showing the variation in leaf shape that can characteristically be found on any one plant of Hawaiian Holly.

Of the commercial cultivars known to the inventor, the most similar in comparison to Hawaiian Holly is the cultivar Moesiana.

Hawaiian Holly is similar to Moesiana in that both cultivars bear small scarlet-red flowers with a darker red eye. Both cultivars propagate easily, have dark green heterophyllus leaves and are resistant to bud drop (shipping tolerance).

Hawaiian Holly differs from Moesiana in that its pot habit is more compact and the plant requires less growth regulator, while Moesiana has very vigorous willowy growth requiring a lot of growth regulator to maintain a compact plant. Hawaiian Holly is very resistant to Bacterial Leaf Spot (Pseudomonas), while Moesiana is highly susceptible.

In the following description, color references are made to The Royal Horticultural Society Colour Chart. The color readings were taken from greenhouse grown plants on Jan. 19, 1989. All readings were taken in an office under cool white fluorescent lights, facing a west window between the hours of 10:00 A.M. and 2:00 P.M.

Classification:

*Botanical.*—*Hibiscus rosa-sinensis L.* cv. Hawaiian Holly.

*Commercial.*—Greenhouse pot crop.

INFLORESCENCE

A. Flower (general):

*Size.*—10 cm.

*Borne.*—In axils of leaves, 1 per node.

*Form.*—Regular single.
*Life.*—1 day.
*Fragrance.*—None.
*Blooming habit.*—Continuously, year round.

B. Corolla (petals):
*Texture.*—Smooth, veins slightly raised.
*Substance.*—Medium thick.
*Shape.*—Rounded.
*Color.*—Eye: Red 45A. Throat: Pink 51A (due to light reflection as throat, color appears much darker). Zone: None. Body of petal: Main veins — pink 51A. Smaller veins — Red 43A. Interveinal — Red 43A. Edge: None.

C. Bud (one day prior to opening):
*Size.*—5.5 cm.
*Shape.*—Cigar shaped.
*Color.*—Veins — Yellow 2C. Interveinal — Red 42A.

D. Calyx: Cup shaped, 5 pointed lobes, a single prominent midvein per lobe, membranous.
*Length.*—3.0 cm.
*Color.*—Veins — Green 144A. Interveinal — Green 145A.

E. Epicalyx: 6–8 pointed, narrow, sword-shaped bracts.
*Length.*—2.0–2.5 cm.
*Color.*—Green 137B.

F. Peduncle:
*Length.*—5.5–6.5 cm.
*Strength.*—Strong.
*Aspect.*—Smooth.
*Color.*—Green 144A.

G. Reproductive organs:

1. *Androecium* (*stamens*).—Anthers: Numerous. Filaments: 0.8 cm., Pink 52C. Pollen: Moderate. Color: Yellow 13A. Staminal column: Upper 33% antheriferous. Length: 6.0 cm. Color: Pink 52C.
2. *Gynoecium* (*pistil*).—Stigma: 5 in number, rounded, discoid, hairy. Color: Red 45A. Style: Length: 7.5 cm. Color: Yellow 5D. Branches: 5 in number. Color: Pink 52C. Ovary: Rounded. Color: Yellow 4C.

PLANT CHARACTERISTICS

A. Foliage:
*Arrangement.*—Alternate.
*Shape.*—Juvenile: Heterophyllus. Mature: Entire, deeply serrate. Color: Dark green 139A.
*Petiole.*—Length: 4.0–4.5 cm. Aspect: Smooth. Color: Green 137A.
*Stipules.*—Two per node, shape acicular (needle shaped). Color: Dark green 139A.

B. Stem: Smooth, becoming woody with age.
C. Plant habit: Excellent, compact.
D. Breaking action: Excellent.
E. Rooting: Excellent.
F. Growth regulator: Very little required.
G. Low light bud initiation: Good.
H. Shipping tolerance: Excellent.

I claim:

1. A new and distinct cultivar of Hibiscus plant named Hawaiian Holly, as described and illustrated.

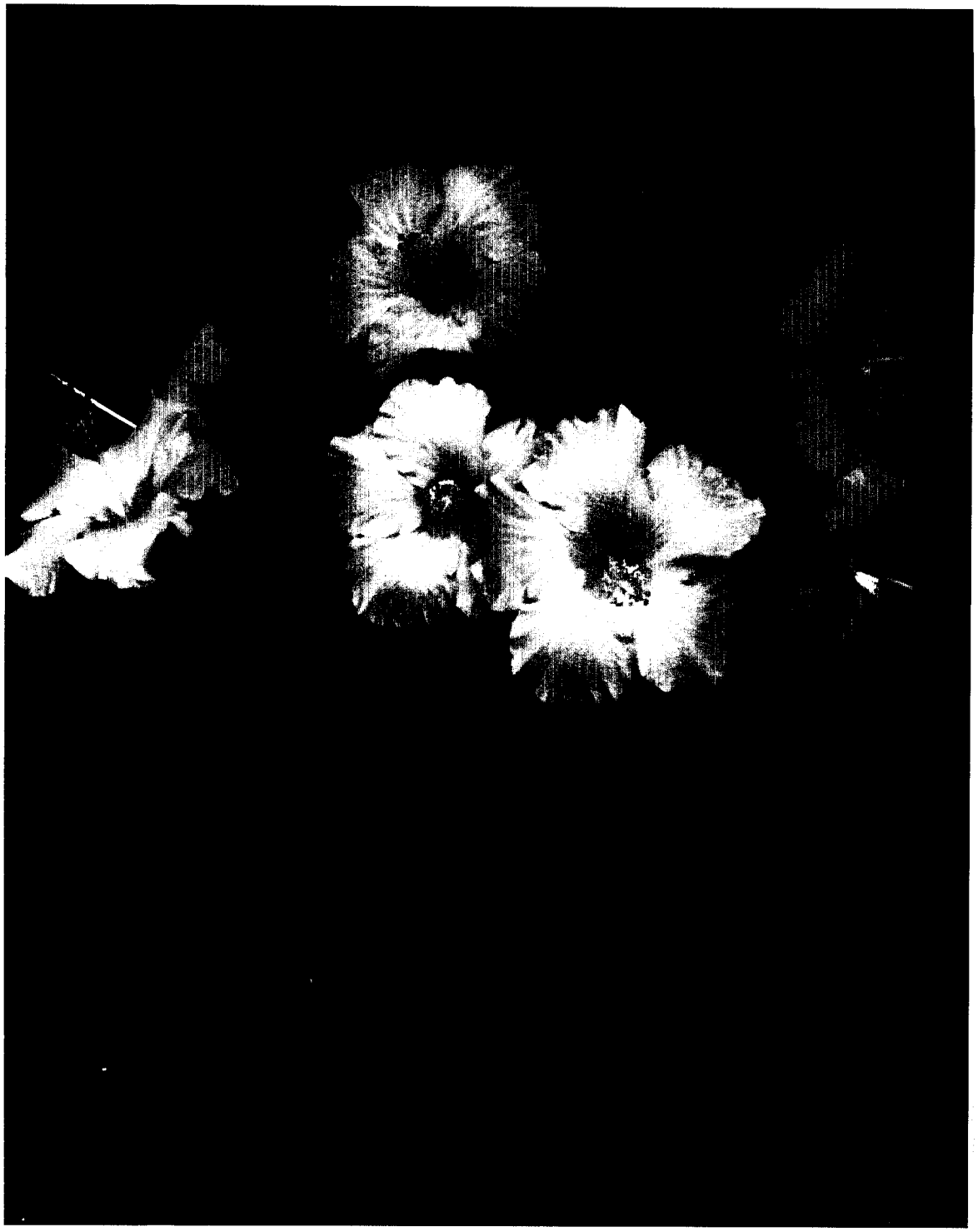

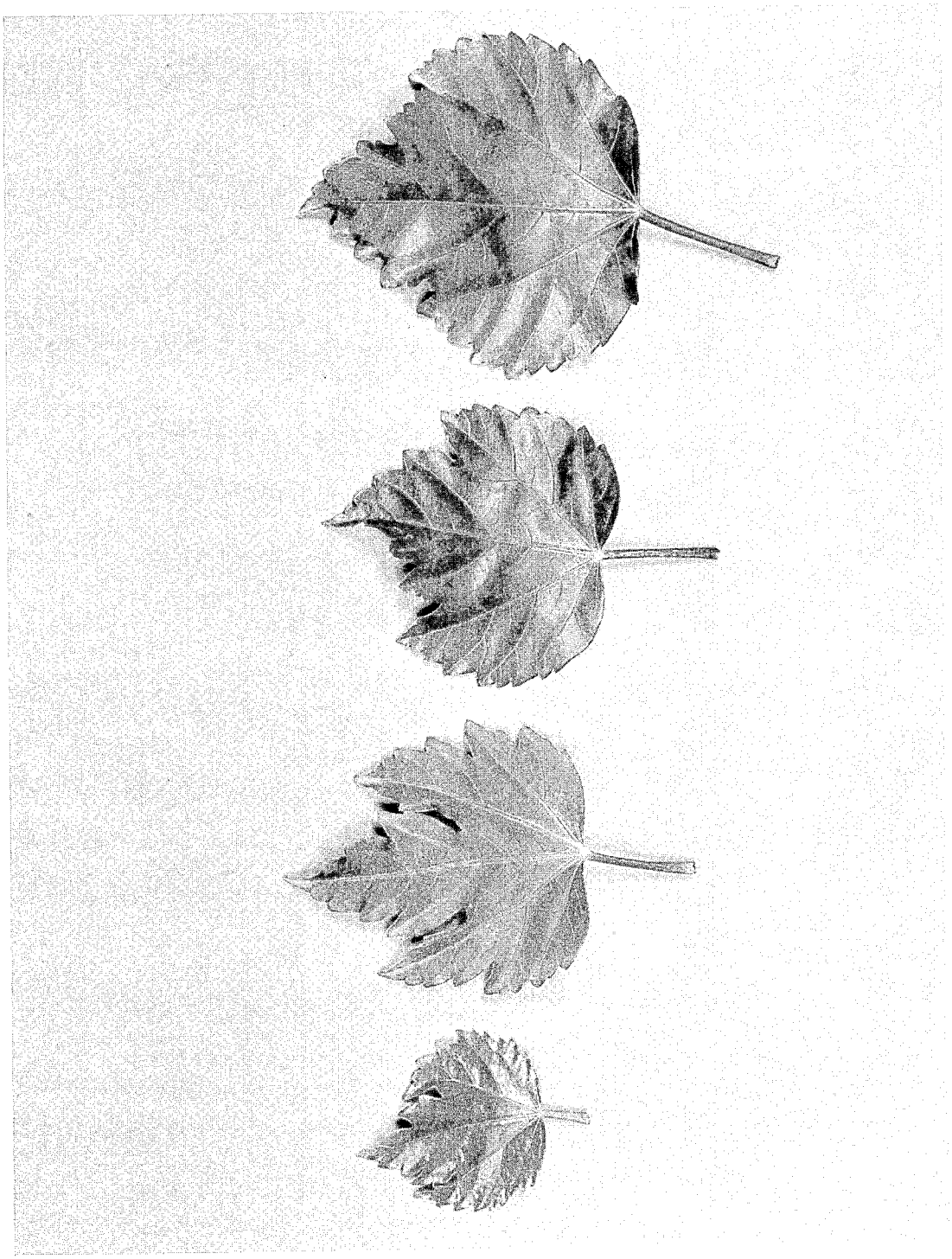

* * * * *